(12) United States Patent
Sumiya (10) Patent No.: US 6,305,803 B2
(45) Date of Patent: Oct. 23, 2001

(54) OPHTHALMIC APPARATUS

(75) Inventor: Toshifumi Sumiya, Nukata-gun (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/779,847

(22) Filed: Feb. 9, 2001

(30) Foreign Application Priority Data

Feb. 10, 2000 (JP) .................................................. 12-32987

(51) Int. Cl.$^7$ ...................................................... A61B 3/10
(52) U.S. Cl. ................................................................ 351/212
(58) Field of Search ................................... 351/211, 212, 351/214, 221, 160 R; 600/587; 606/4, 5, 11, 12; 359/653, 654; 356/124, 124.5, 125, 127

(56) References Cited

U.S. PATENT DOCUMENTS

| | | |
|---|---|---|
| 5,500,697 | 3/1996 | Fujieda . |
| 5,582,185 | * 12/1996 | Ediger et al. .......................... 600/587 |
| 5,637,109 | 6/1997 | Sumiya . |
| 5,800,424 | 9/1998 | Sumiya . |
| 5,906,608 | 5/1999 | Sumiya et al. . |
| 6,033,075 | 3/2000 | Fujieda et al. . |
| 6,089,711 | * 7/2000 | Blankenbecler et al. ........ 351/160 R |
| 6,126,286 | * 10/2000 | Portney ............................ 351/160 R |

OTHER PUBLICATIONS

Kawahara, T., "Refractive Power Correction and Modulation Transfer Function (MTF)", *Ophthalmology Mook*, Kanehara Shuppan Kabushiki Kaisha, No. 18 (1992), pp. 108–109.

Kawahara, T., "New Method of Examination–Modulation Transfer Function and Visual Function," *Ophthalmology 23*, Kanehara Shuppan Kabushiki Kaisha (1981), pp. 1045–1046 & pp. 1047–1049.

Kawahara, T., "Refractive Power Correction and Modulation Transfer Function (MTF)", *Ophthalmology Mook*, Kanehara Shuppan Kabushiki Kaisha, No. 18 (1982), p. 101.

Kondo, F., Lens Design Schemes (Lenzu no Sekkei Giho), Kogaku Kogyo Gijutsu Kyokai (1978), p. 293, line 18—p. 294, line 11.

* cited by examiner

*Primary Examiner*—George Manuel
(74) *Attorney, Agent, or Firm*—Finnegan, Henderson, Farabow, Garrett & Dunner, L.L.P.

(57) ABSTRACT

An ophthalmic apparatus used in refractive surgery for changing a radius of curvature of a cornea, the apparatus comprising a first input device for inputting data about a pre-operative corneal shape of a patient's eye, a second input device for inputting data about an intended post-operative corneal shape of the eye, a third input device for inputting data about a pre-operative MTF of an ocular imaging system of the eye, and an arithmetic device for obtaining an intended post-operative MTF of the ocular imaging system of the eye based on each inputted data.

22 Claims, 8 Drawing Sheets

OPHTHALMIC APPARATUS

BACKGROUND OF THE INVENTION

1. Field of the Invention

The present invention relates to an ophthalmic apparatus. More particularly, the present invention relates to an ophthalmic apparatus used in refractive surgery to change (alter) a radius of curvature of a cornea of a patient's eye by corneal ablation.

2. Description of Related Art

There are several types of refractive surgery to change (alter) a radius of curvature of a cornea of a patient's eye by ablating the cornea with an excimer laser beam thereby to correct refractive errors such as myopia, hyperopia, astigmatism and the like. Conventionally, in such types of surgery, the corneal shape, the eye refractive power of the eye and the like are measured before an operation and then the operation is carried out based on the obtained measurement data.

However, in these types of surgery, attention has been paid merely to correction of the refractive power of optics of the eye such that a paraxial focal points is positioned on the retina and quality of the image formed on the retina (influence of marginal rays on the image) has not been taken into account. Therefore, the corneal ablation may not necessarily be carried out properly and patients may not be fully satisfied with their post-operative visions.

In addition, although a radius of curvature of the cornea is properly corrected thereby achieving emmetropization of the optics of the eye, the patient may not always improve the post-operative vision as he expected in case the patient suffers from a disturbance in the nervous system following the retina, the brain or other signal system. Therefore, it is desirable to give sufficient information to a patient and to make him fully understand of the situation before performing surgery.

SUMMARY OF THE INVENTION

The present invention has been made in view of the above circumstances and has an object to overcome the above problems and to provide an ophthalmic apparatus which allows that corneal ablation is carried out in consideration of quality of an image on a retina, and the post-operative state of the patient's eye is estimated.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic apparatus used in refractive surgery to change a radius of curvature of a cornea, the apparatus comprises first input means for inputting data about a pre-operative corneal shape of a patient's eye, second input means for inputting data about an intended post-operative corneal shape of the eye, third input means for inputting data about a pre-operative MTF of an ocular imaging system of the eye, and arithmetic means for obtaining an intended post-operative MTF of the ocular imaging system of the eye based on each inputted data.

In another aspect of the present invention, an ophthalmic apparatus used in refractive surgery to change a radius of curvature of a cornea, the apparatus comprises a corneal shape analysis unit which obtains data about a corneal shape of a patient's eye, an MTF measurement unit which obtains data about an MTF of a visual system and data about an MTF of a retina-brain system of the eye, an input unit which inputs data about an intended post-operative corneal shape of the eye, and an arithmetic unit. The arithmetic unit is used to obtain: a pre-operative MTF of the cornea of the eye based on the obtained data about a pre-operative corneal shape; a pre-operative MTF of an ocular imaging system of the eye based on the obtained data about a pre-operative MTF of the visual system and the obtained data about a pre-operative MTF of the retina-brain system; a pre-operative MTF of an intraocular optical system of the eye based on the obtained pre-operative MTF of the cornea and the obtained pre-operative MTF of the ocular imaging system; an intended post-operative MTF of the cornea of the eye based on the inputted data about the intended post-operative corneal shape; and an intended post-operative MTF of the ocular imaging system of the eye based on the obtained pre-operative MTF of the intraocular optical system and the intended post-operative MTF of the cornea obtained thereby.

Yet, in another aspect of the present invention, an ophthalmic apparatus used in refractive surgery to change a radius of curvature of a cornea, the apparatus comprises a memory and an arithmetic unit which performs arithmetic operation in accordance with the program. The memory contains a program therein for obtaining an intended post-operative MTF of an ocular imaging system of the eye based on data about a pre-operative corneal shape, data about an intended post-operative corneal shape and data about a pre-operative MTF of the ocular imaging system of the eye.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
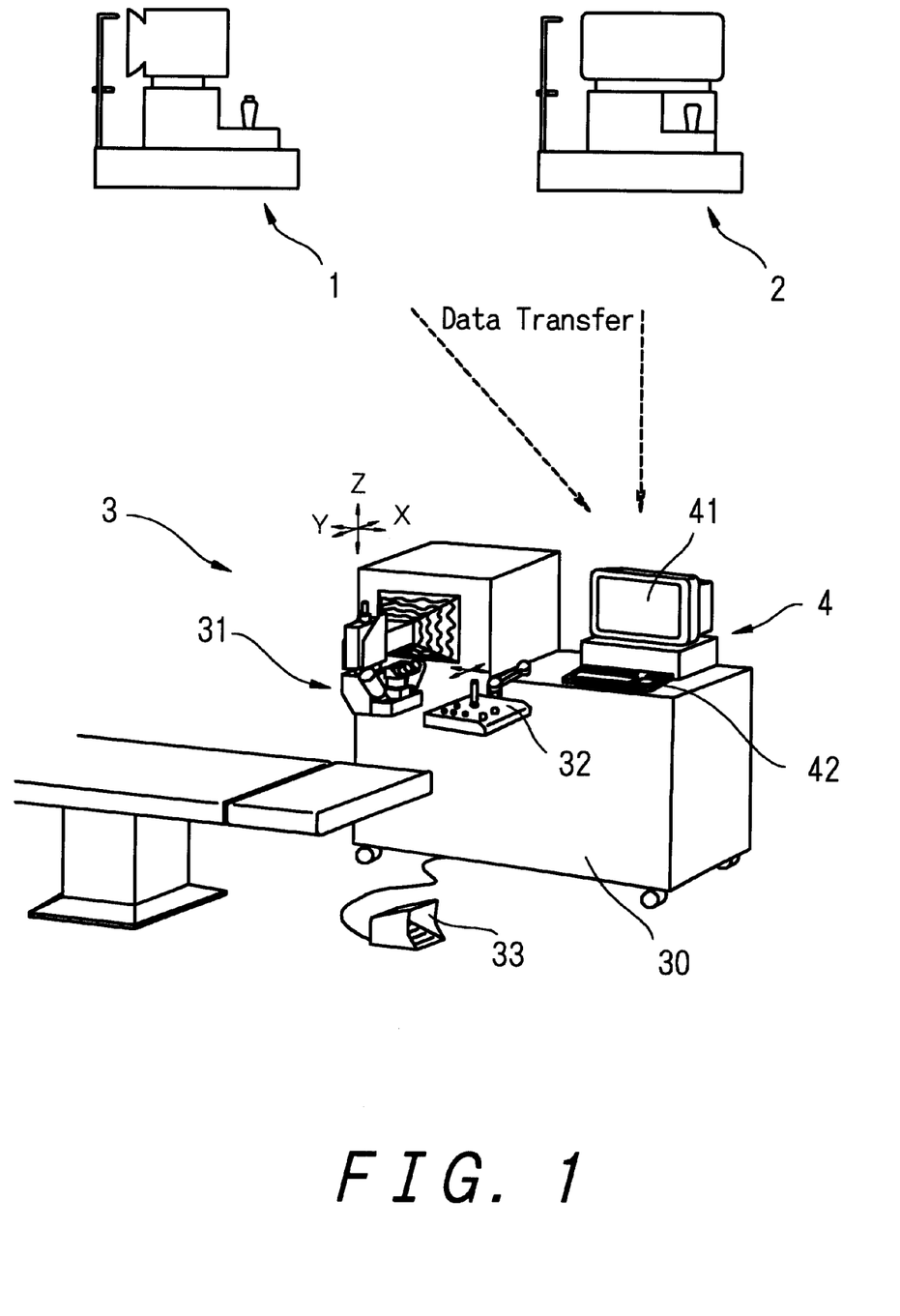
FIG. 1 is a view showing a schematic configuration of an ophthalmic apparatus of one preferred embodiment consistent with the present invention.

A detailed description of one preferred embodiment of an ophthalmic apparatus embodying the present invention will now be given referring to the accompanying drawings. FIG. 1 is a view showing a schematic configuration of an ophthalmic apparatus (an ophthalmic system) of this preferred embodiment.

Reference numeral 1 is a corneal shape analysis apparatus for measuring a corneal shape and an eye refractive power of a patient's eye. 2 is an MTF measurement apparatus for measuring Modulation Transfer Functions (hereinafter referred to as MTF). 3 is a corneal surgery apparatus for performing eye refractive surgery to ablate the cornea with an excimer laser beam having a 193 nm wavelength. 4 is a computer unit, comprising a display monitor 41 and a keyboard 42, for inputting necessary data for surgery, calculating the ocular imaging system MTF, calculating corneal ablation data and the like (described in detail later). Hereinafter, the corneal shape analysis apparatus 1, the MTF measurement apparatus 2 and the corneal surgery apparatus 3 will be described separately.

<Corneal Shape Analysis Apparatus>

Figure 2:
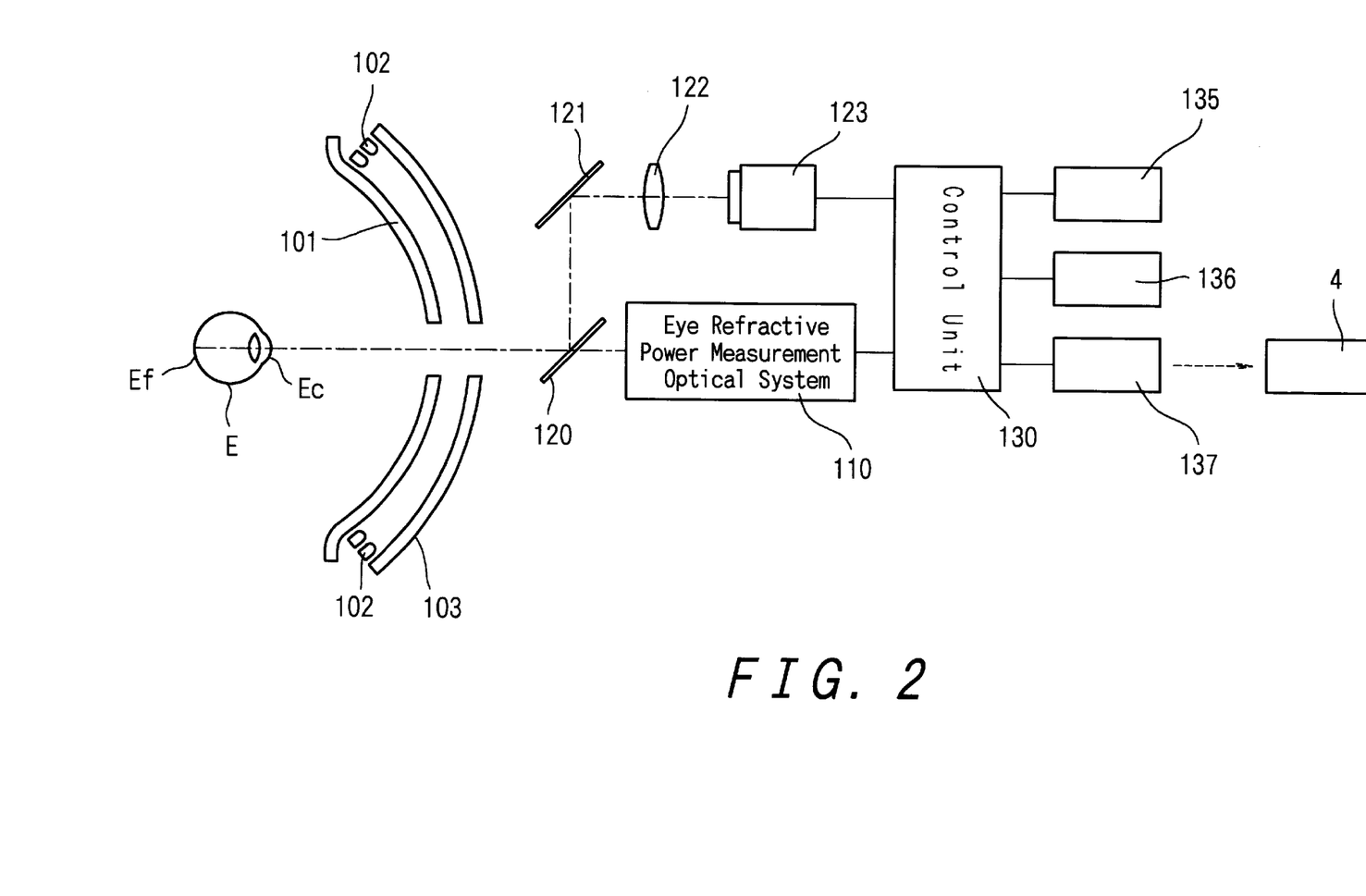
FIG. 2 is a view showing a schematic configuration of an optical system and a control system included in a corneal shape analysis apparatus used in the ophthalmic apparatus shown in FIG. 1.

FIG. 2 is a view showing a schematic configuration of an optical system and a control system of the corneal shape analysis apparatus 1. Light emitted from an illumination light source 102 is reflected by a reflecting plate 103 so as to illuminate a placid plate 101 in which numerous ring patterns are formed thereon from behind generally uniformly. As the result, an image of the ring pattern is formed (projected) onto a cornea Ec of a patient's eye E. The image of the ring pattern is photographed by a CCD camera 123 via a beam splitter 120, a mirror 121 and a lens 122. A control unit 130 conducts image processing on the image of the ring pattern photographed by the camera 123 to obtain curvature distribution (distribution of the radius of curvature) through detecting edges of the ring pattern image. In this manner, the corneal shape of the eye E which equally means the corneal topography is obtained.

Further, an eye refractive power measurement optical system 110 is disposed at the back (on the transmitting side) of the beam splitter 120. In the measurement optical system 110, measurement light is projected onto a fundus Ef of the eye E and reflected light from the fundus Ef is detected by a photodetector. The control unit 130 obtains the eye refractive power of the eye E (spherical power S, cylindrical power C, astigmatic axial angle A) based on an output signal from the photodetector.

Each of the thus obtained data about the corneal shape and the eye refractive power of the eye E is stored in a memory 135. In response to a signal from a transfer switch 136, each obtained data is transferred to the computer unit 4 via an output unit 137.

Here, for such a corneal shape analysis apparatus having an eye refractive power measurement function, the one disclosed in U.S. Pat. No. 6,033,075 (Japanese Unexamined Patent Publication No. HEI 11-276437) maybe applicable. Alternatively, two separate apparatuses: one for measuring corneal shape and the other for measuring eye refractive power are of course applicable.

<MTF Measurement Apparatus>

Figure 3:
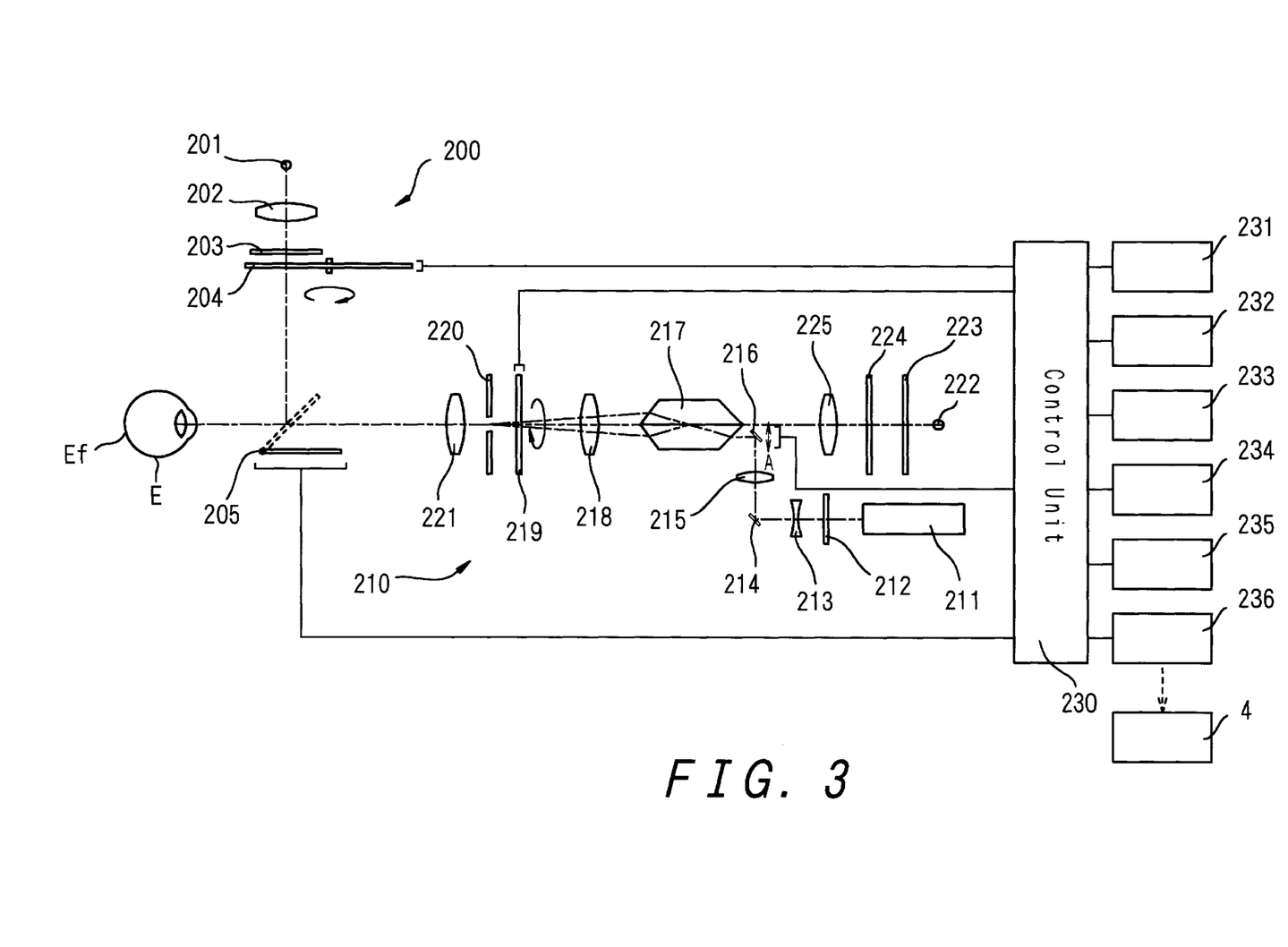
FIG. 3 is a view showing a schematic configuration of an optical system and a control system included in a Modulation Transfer Function (MTF) measurement apparatus used in the ophthalmic apparatus shown in FIG. 1.

FIG. 3 shows a schematic configuration of an optical system and a control system of the MTF measurement apparatus 2. The MTF measurement apparatus 2 comprises a visual system MTF measurement system 200 for measuring the visual system MTF, and a retina-brain system MTF measurement system 210 for measuring the retina-brain system MTF. A pop-up mirror allows a measurement light path (optical path) of each measurement system to be changed.

Here, description is given to the MTF of perception. The MTF of perception is one scheme to quantitatively express quality of a perceived image of an external object, and expresses how well the patient (the examinee) perceives the presented fringe target. Specifically, to obtain the MTF, fringe target formed out of stripes of light and dark with various pitches are presented at various contrasts, and discriminating ability regarding the presented fringe target is examined.

Figure 6:
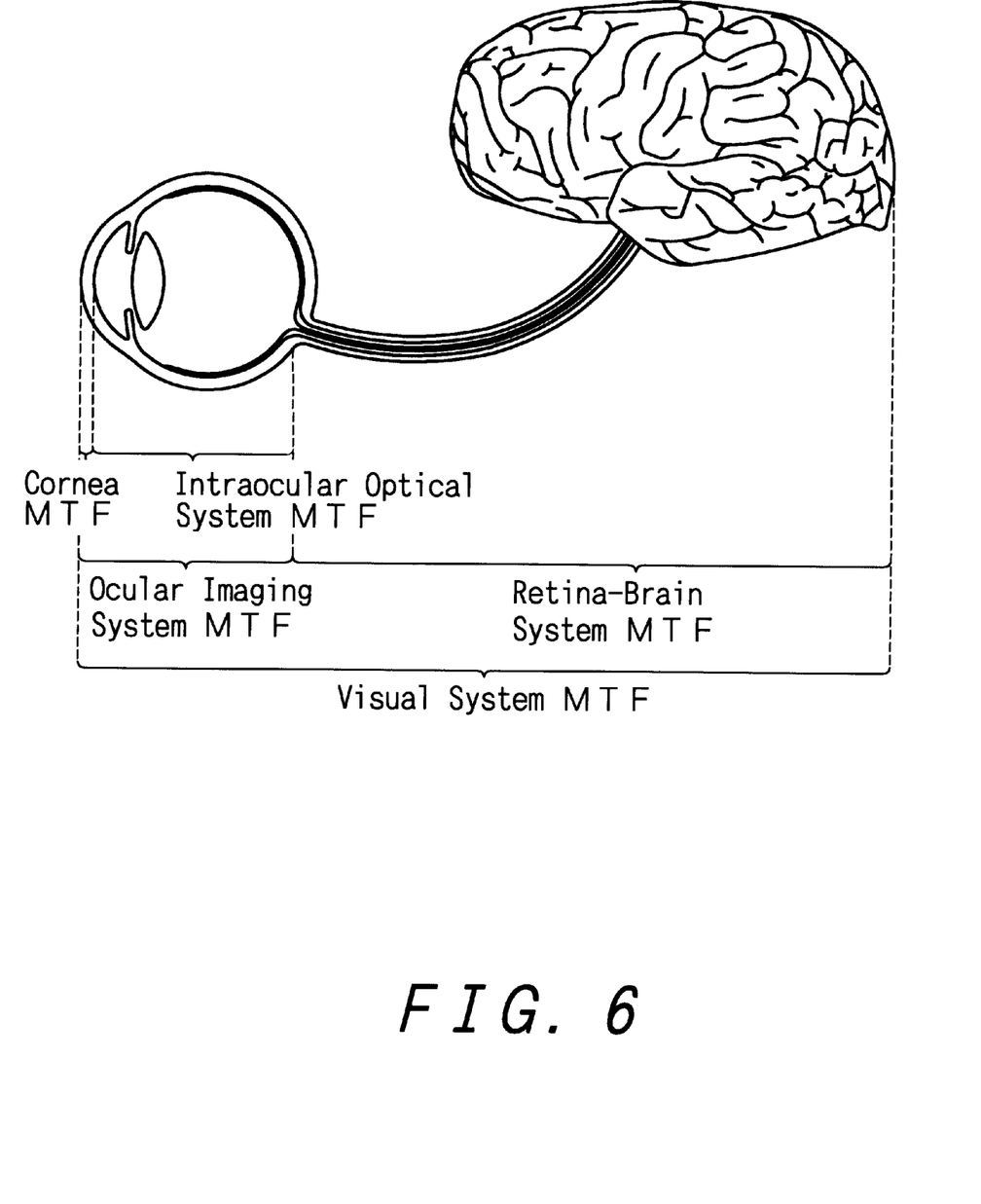
FIG. 6 is a view showing a relation among each MTF.

As shown in FIG. 6 explaining the relation among each MTF, in this preferred embodiment, the ocular imaging system MTF is intended to mean the MTF of the ocular imaging system including the cornea, the crystalline lens, the vitreous body and the like. Further, the ocular imaging system MTF includes the cornea MTF indicating the MTF of the imaging function of the cornea alone and the intraocular optical system MTF indicating the MTF of the imaging system other than the cornea (namely, the crystalline lens, the vitreous body and the like). The MTF of the nervous system and the signal system following the retina (perception by the brain) is denoted as the retina-brain system MTF (the retina-brain system MTF expresses how well the image formed on the retina is perceived). The MTF of the whole visual system including the ocular imaging system MTF and the retina-brain system MTF is denoted as the visual system MTF (the visual system MTF expresses how well the patient perceives a presented target).

Here, it is known that the visual system MTF ($M_V(u)$) is the product of the ocular imaging system MTF ($M_O(u)$) and the retina-brain system MTF ($M_N(u)$) as expressed in the following expression (1).

$$M_V(u)=M_O(u) \cdot M_N(u) \tag{1}$$

Figure 7:
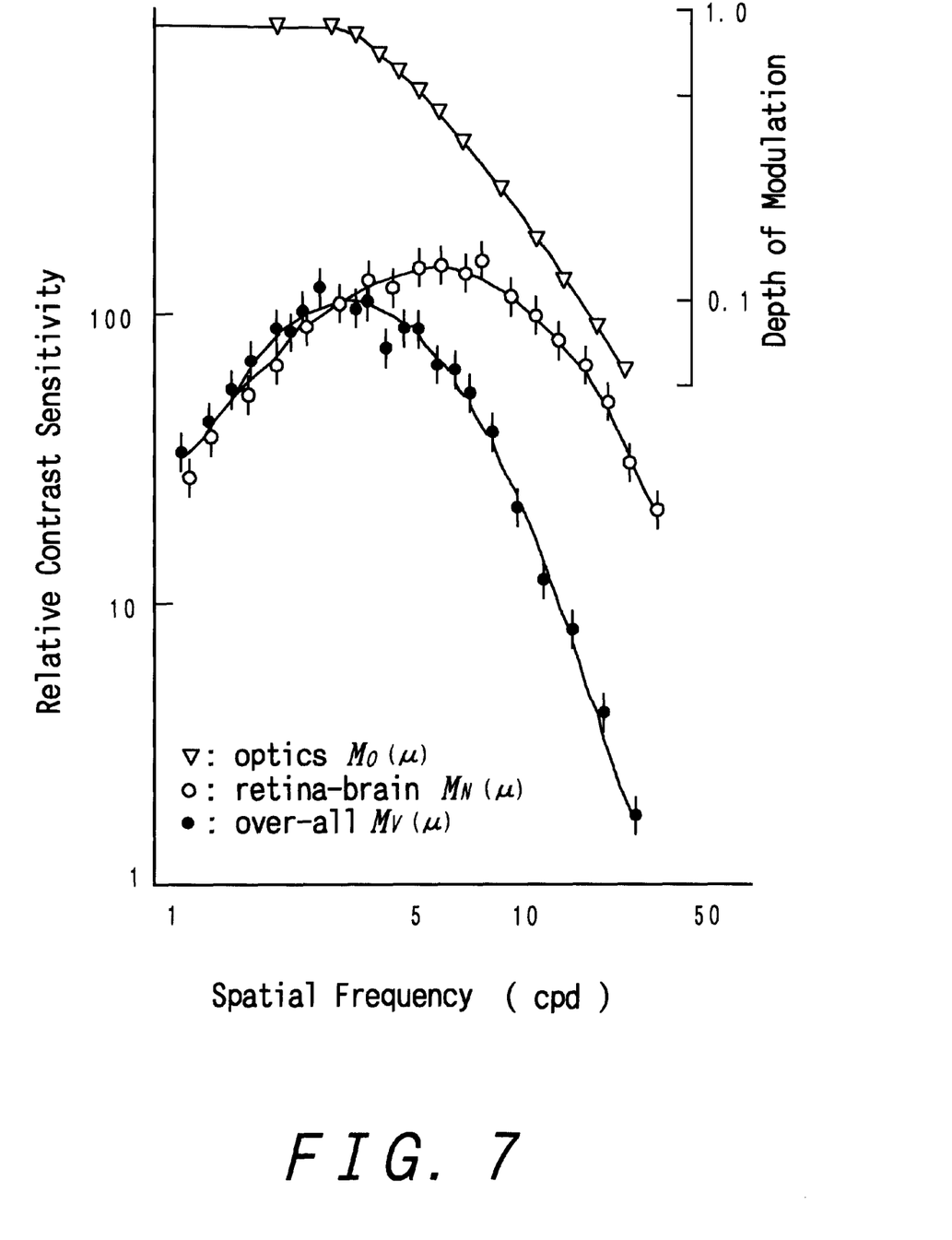
FIG. 7 is a view showing a relation among the visual system MTF, the retina-brain system MTF and the ocular imaging system MTF.

So, if the visual system MTF and the retina-brain system MTF are measured respectively and the ocular imaging system MTF is obtained using the expression (1), the relation is as shown, for example, in FIG. 7.

Further, the ocular imaging system MTF ($M_O(u)$) is the product of the cornea MTF ($M_C(u)$) and the intraocular optical system MTF ($M_I(u)$) and this relation is expressed in the following expression (2).

$$M_O(u)=M_C(u) \cdot M_I(u) \tag{2}$$

In FIG. 3, the visual system MTF measurement system 200 is constituted from an illumination light source 201 for target projection, a condenser lens 202, a diffusing plate 203 and a rotary target plate 204 having numerous fringe targets with different fringe pitches and different contrasts. When the MTF measurement apparatus 2 goes into a visual system MTF measurement mode by a measurement switch 231, the mirror 205 is inserted into the optical path so that a fringe target of the target plate 204 is illuminated by the light source 201 and presented to the eye E. The control unit 230 rotates the target plate 204 to present fringe targets of different pitches and different contrasts one by one to the patient. The patient is instructed to input using a response switch 233 as to whether he can see a presented fringe target. Based on the presented target and an input signal from the switch 233, the control unit 230 calculates a discrimination threshold and then obtains the visual system MTF (for example, $M_V(u)$ shown in FIG. 7).

In the retina-brain system MTF measurement system 210, a laser beam emitted from a He-Ne laser source 211 passes through a polarizing plate 212, an expander lens 213, a mirror 214, a lens 215 and a scanning mirror 216, and then enters into a prism beam splitter 217. Thereafter, the laser beam is divided into two beams of light by the beam splitter 217. The two beams of light converges via a lens 218, an analyzer 219, an aperture 220 and a lens 221 in the vicinity of the pupil of the eye E, and is brought into one again on the fundus Ef. As such, by making the two laser beams coincide with each other, interference occurs and a sinusoidal fringe pattern (fringe target) is produced. The distance between the two beams of light changes by moving the scanning mirror 216 in the direction of the arrow A, and therefore the interference fringes serving as the fringe target can be changed the pitch of the fringes.

Further, incoherent light emitted from a tungsten lamp 222 passes through a filter 223, a polarizing plate 224 and a lens 225 and then enters into the beam splitter 217. Thereafter, the incoherent light passes though the lens 218, the analyzer 219, the aperture 220 and the lens 221 to illuminate the fundus Ef uniformly. The filter 223 has a characteristic that transmits light having the same wavelength as that of the laser beam emitted from the laser source 211. Hence, the light emitted from the lamp 222 illuminating the eye E is limited to the light having the same wavelength as that of the laser beam. The polarizing plates 212 and 224 have polarizing planes which are perpendicular to each other. Therefore, by rotating the analyzer 219, the light from the lamp 222 overlaps so that the contrast of the fringe target can be changed arbitrarily.

When the MTF measurement apparatus 2 goes into a retina-brain system MTF measurement mode by a measurement switch 232, the mirror 205 is removed from the optical path. The control unit 230 moves the scanning mirror 216 to change the fringe pitch of the fringe target and rotates the analyzer 219 to change the contrast of the fringe target. In this way, the eye E is presented various fringe targets at various fringe pitches and various contrasts one by one. The patient is instructed to input using the response switch 233 as to whether the fringe target is perceptive to him. The control unit 230 then calculates a discrimination threshold and obtains the retina-brain system MTF based on the presented target and the input signal from the switch 233 (for example, $M_N(u)$ shown in FIG. 7). In the case of this measurement, the fringe target formed on the retina is free from influence of the imaging operation by the ocular imaging system so that function of the systems following the retina can be solely evaluated.

The obtained data about the visual system MTF and the retina-brain system MTF are stored into a memory 234. Then, in response to a signal from a transfer switch 235, each obtained data is transferred to the computer unit 4 via an output unit 236.

<Corneal Surgery Apparatus>

Figure 4:
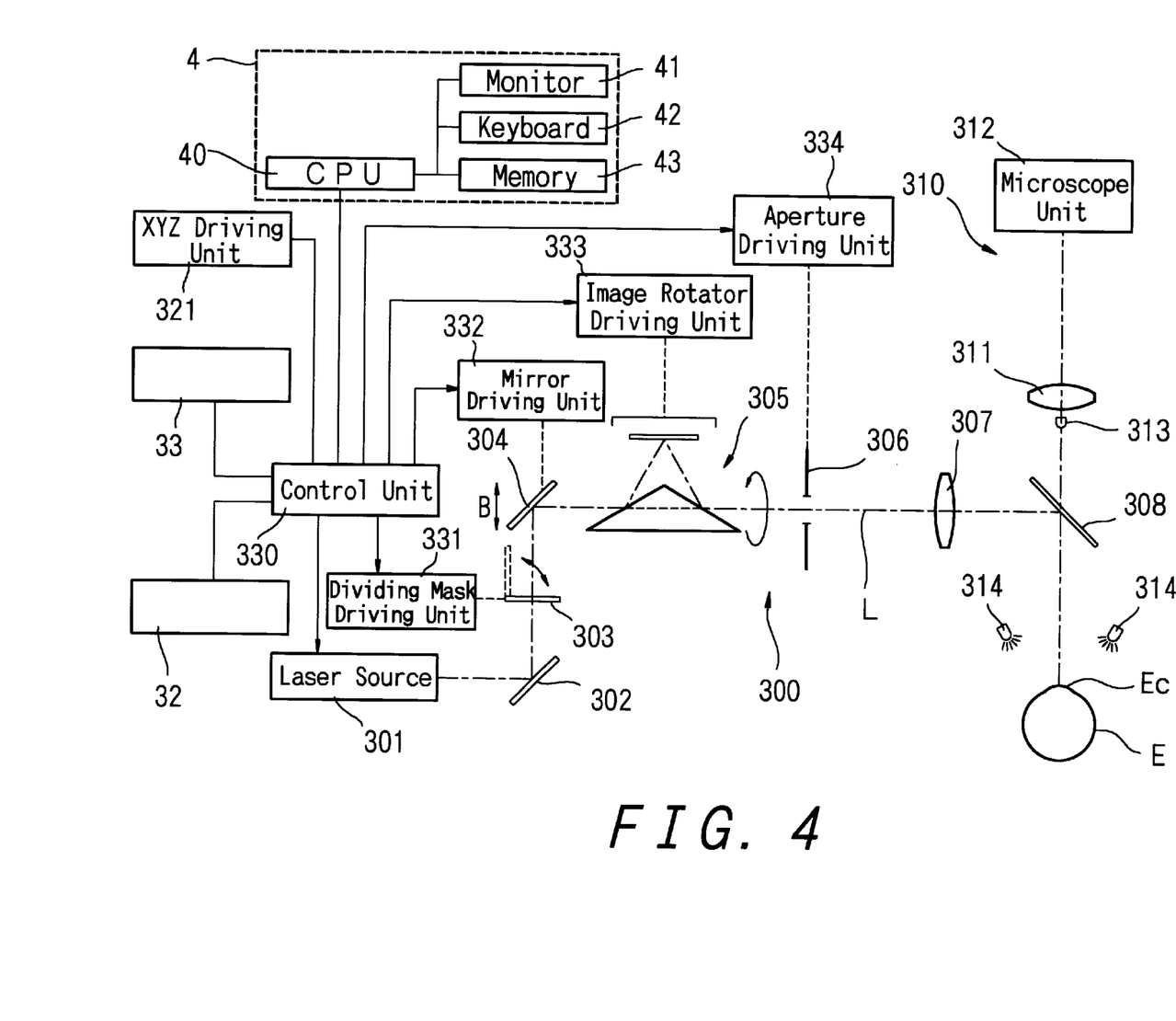
FIG. 4 is a view showing a schematic configuration of an optical system and a control system included in a corneal surgery apparatus used in conjunction with the ophthalmic apparatus shown in FIG. 1.

Now, the configuration of the corneal surgery apparatus 3 is described with reference to FIGS. 1 and 4. FIG. 4 is a view showing an optical system and a control system of the corneal surgery apparatus 3.

Reference numeral 30 is the main body of the surgery apparatus with an excimer laser source 301 installed therein. An excimer laser beam emitted from the laser source 301 is directed to an arm unit 31. The arm unit 31 comprises a part of a laser irradiation optical system 300 and an observation optical system 310 installed therein, and is moved in a right and left (X) direction and a back and forth (Y) direction relative to an operator by an XYZ driving unit 321. Also, the tip portion of the arm unit 31 having a laser irradiation exit is moved in an up and down (Z) direction by the XYZ driving unit 321. 32 is a controller having a joystick and switches for moving the arm unit 31 and its tip portion. The XYZ driving unit 321 is activated in response to a signal from the joystick or the switches. 33 is a foot switch for issuing a signal for triggering laser irradiation.

In FIG. 4, reference numeral 300 is the laser irradiation optical system. An excimer laser beam (wavelength 193 nm) emitted from the laser source 301 is reflected by a mirror 302, and reflected again by a scanning mirror 304 via a dividing mask 303 which are numerous strip-shaped masks placed one next to another. Thereafter, the excimer laser beam goes through an image rotator 305, a variable circular aperture 306 and a projecting lens 307, and then is reflected by a dichroic mirror 308 to irradiate the cornea Ec.

The mirror 304 may be moved in a direction of the arrow B by a mirror driving unit 332, and the rotator 305 is rotated about an optical axis L by an image rotator driving unit 333. Movement of the mirror 304 and rotation of the rotator 305 allow the excimer laser beam to be scanned over the cornea Ec. Further, the aperture 306 and the cornea Ec are in a conjugate positional relation relative to the lens 307. Thus, an opening region of the aperture 306 that is changed by an aperture driving unit 334 forms an image on the cornea Ec, thereby limiting an ablation area (a laser irradiation area).

In the case of spherical correction for myopia, movement of the mirror 304 and the opening diameter of the aperture 306 are controlled so as to ablate the cornea Ec more at the center and less at the periphery (the ablation depth is made gradually shallower from the center toward the periphery). Thus, the radius of curvature of the cornea Ec is enlarged at the predetermined area (the ablated area) (See U.S. Pat. No. 5,637,109 (Japanese Unexamined Patent Publication No. HEI 5-220189) for reference). On the contrary, in the case of spherical correction for hyperopia, the mirror 304 and the rotator 305 are controlled (here, the opening diameter of the aperture 306 remains unchanged) so as to ablate the cornea Ec less at the center and more at the periphery (the ablation depth is made gradually deeper from the center toward the periphery). Thus, the radius of curvature of the cornea Ec is reduced at the predetermined area (the ablated area) (See U.S. Pat. No. 5,800,424 (Japanese Unexamined Patent Application No. HEI 8-66420) for reference). Further, in the case of ablating an asymmetric component, open/close of each strip-shaped mask constituting the dividing mask 303 and the movement of the mirror 304 are controlled so as to selectively ablate uneven surface of the cornea Ec (See U.S. Pat. No. 5,906,608 (Japanese Unexamined Patent Publication No. HEI 9-266925) for reference).

Reference numeral 310 is the observation optical system comprising an objective lens 311 and a surgical microscope unit 312 of a binocular type. Disposed on the optical axis of the lens 311 is a fixation light 313. 314 is a visible light source for illumination.

Hereinafter, description will be given mainly to operations for obtaining corneal ablation data using an apparatus having the configuration as above.

First, each measurement data, namely the data about pre-operative corneal shape obtained by the corneal shape analysis apparatus 1 and the data about the pre-operative MTFs of the visual system and the retina-brain system obtained by the MTF measurement apparatus 2, is inputted to the computer unit 4. In addition, correction amount data (S, C and A) required for emmetropization of the eye E are inputted using the key board 42. The correction amount data may be eye refractive power measurement data obtained by using the corneal shape analysis apparatus 1 or through subjective measurement. The corneal shape data, each of the MTF data and the correction amount data, all of which are inputted to the computer unit 4 are stored into the memory 43 provided therein and read therefrom and used as necessary. The CPU 40 of the computer unit 4 carries out analysis on each data to obtain corneal ablation data.

Figure 5A:
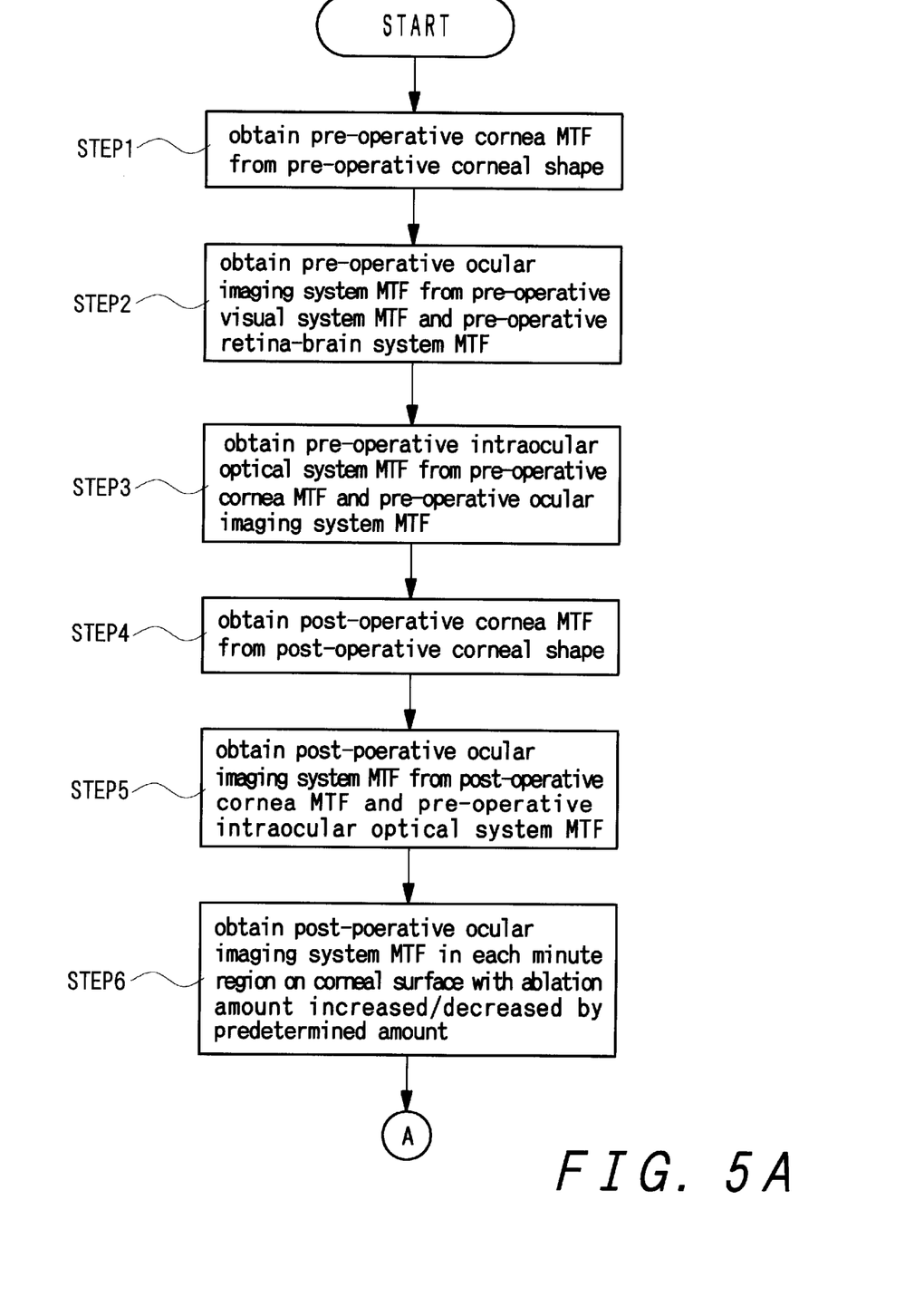
FIGS. 5A and 5B are a flow chart showing steps to obtain an intended post-operative MTF of a patient's eye.
Figure 5B:
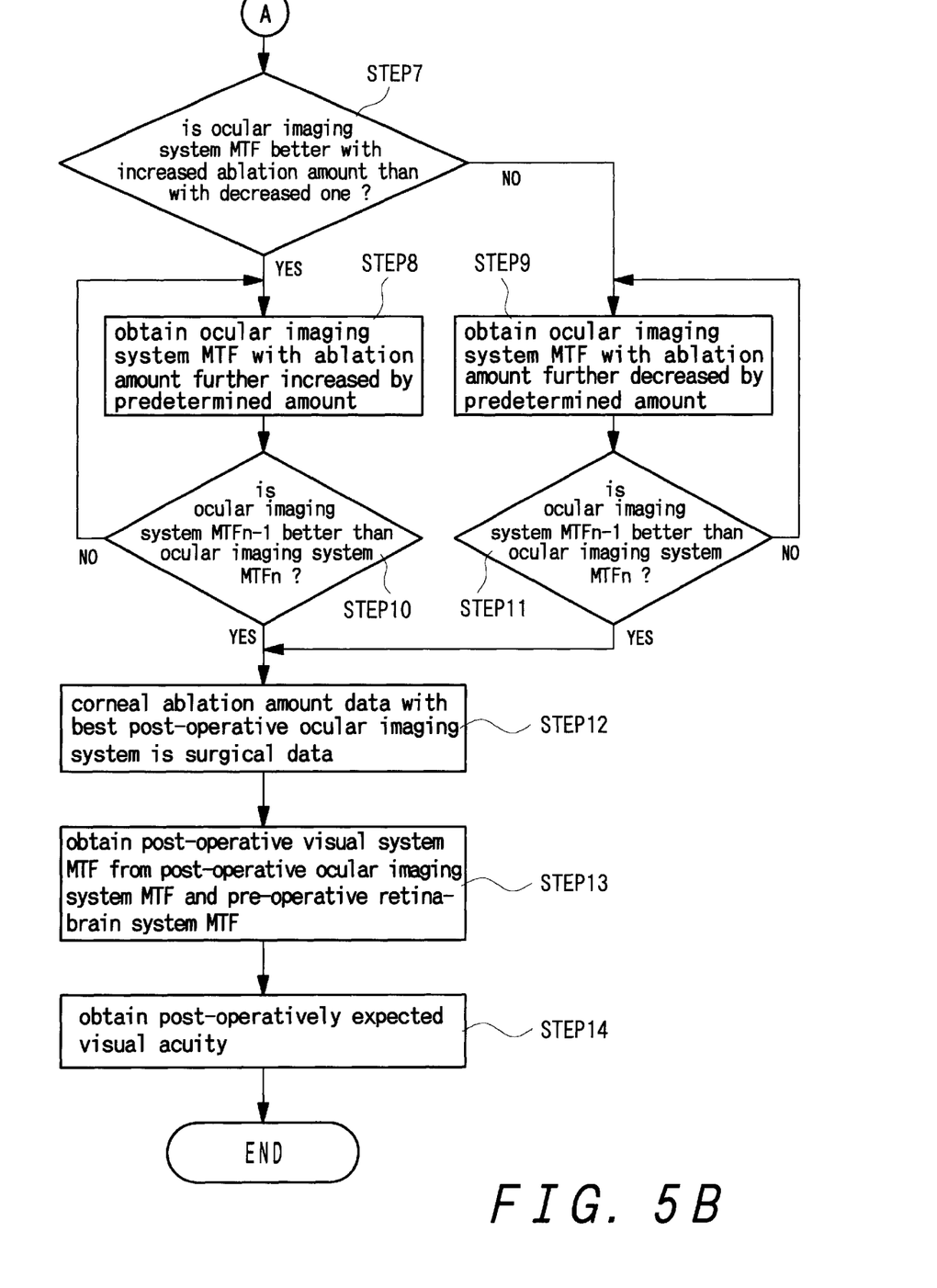

Hereinafter, description is given to the analysis operation that the computer unit 4 (the CPU 40) performs with reference to the flow chart shown in FIGS. 5A and 5B.

To find out about the post-operative condition of the eye E, the operator operates the key board 42 and starts an analysis program stored in the memory 43. Then, the CPU 40 estimates the post-operative MTF of the eye E based on pre-operative corneal shape data and the pre-operative MTF data stored in the memory 43. The post-operative MTF of the eye E is obtained in the following manner.

First, the pre-operative cornea MTF regarding refraction of the corneal surface is obtained from the pre-operative corneal shape data (STEP 1). This pre-operative cornea MTF may be obtained through a known calculation scheme used in optical engineering and the like. In this preferred embodiment, the cornea MTF is obtained, for example, in the following manner: Wave aberration is obtained by ray tracing, a pupil function is applied, then Fourier transformation is performed thereby to obtain the Point Spread Function (PSF) or the Line Spread Function (LSF), and Fourier transformation is further performed to obtain the MTF. There are some other known schemes. One example is that wave aberration is obtained by ray tracing, a pupil function is applied and then the wave aberration MTF is obtained using the auto-correlation. Another example is that, geometric aberration is obtained by ray tracing, a spot diagram is made, and then the geometric MTF is obtained through Fourier transform. (See "Lens Design Schemes (lenzu no sekkei gihou)" by Fumio KONDO (1978), from page 293, line 18 to page 294, line 11 and page 295 for reference.)

Next, the pre-operative ocular imaging system MTF is obtained from the data about the pre-operative visual system MTF and the pre-operative retina-brain system MTF (STEP 2). That is to say, with reference to the above expression (1), once the visual system MTF and the retina-brain system MTF are obtained, the ocular imaging system MTF can be obtained easily.

Further, the pre-operative intraocular optical system MTF is obtained from the thus obtained pre-operative cornea MTF and the thus obtained pre-operative ocular imaging system MTF (STEP 3). That is to say, with reference to the above expression (2), once the ocular imaging system MTF and the cornea MTF are obtained, the intraocular optical system MTF is also obtained easily.

In addition, in order to bring (to position) the focal point on the retina, what needs to be obtained is data about the intended post-operative corneal shape provided that the cornea is ablated according to the correction amount data (hereinafter, this data is referred to as the standard data about the post-operative corneal shape required for focusing) For example, corneal refractive power data are obtained from the pre-operative corneal shape data (the data about radius of curvature of the cornea) using the Snell's law. Then, the sum of the eye refractive power data inputted as the correction amount data and the obtained corneal refractive power data allows to obtain "a value of the refractive power required for emmetropization of the patient's eye in terms of a corneal refractive power" (equally meaning "the equivalent of emmetropia corneal refractive power data"). Then, the obtained equivalent of emmetropia corneal refractive power data are subjected to apply the Snell's law so as to obtain the post-operative corneal shape data (the data about radius of curvature of the cornea) (See, for example, U.S. Pat. No. 6,033,075 for detail). Thereafter, from the standard data about the post-operative corneal shape, the post-operative cornea MTF (the intended post-operative cornea MTF) are obtained using the above calculation scheme for MTF (STEP 4).

Since the pre-operative intraocular optical system MTF is considered to remain unaffected by surgery, the post-operative ocular imaging system MTF (the intended post-operative ocular imaging system MTF) can be obtained from the obtained pre-operative intraocular optical system MTF and the obtained post-operative cornea MTF by using the above expression (2) (STEP 5).

Next, the standard data about the corneal shape are corrected in such a manner to optimize the post-operative ocular imaging system MTF, that is, to make an image formed on the post-operative retina finest. This is done in the following manner.

First, regarding the standard data about the corneal shape, the corneal surface is divided into minute regions. In a minute region, the corneal ablation amount is increased or decreased by a predetermined amount to obtain the post-operative ocular imaging system MTF that will be acquired by ablating the changed amount (STEP 6). Thereafter, it is determined whether the change causes a better outcome (STEP 7). Here, the post-operative ocular imaging system MTF under this condition is obtained by obtaining the post-operative cornea MTF in the same manner as above. Then, the post-operative ocular imaging system MTF is obtained again by further changing (increasing or decreasing) the corneal ablation amount by a predetermined amount in a manner to make a better outcome (STEPS 8 and 9). Then, comparison is made between the two MTFs of the post-operative ocular imaging system: One under the condition where the corneal ablation amount is further changed (hereinafter referred to as the post-operative ocular imaging system $MTF_n$.) and the ocular imaging system MTF that has been obtained before the $MTF_n$. (hereinafter referred to as the post-operative ocular imaging system $MTF_{n-1}$). (STEPS 10 and 11). Here, if the post-operative ocular imaging system $MTF_{n-1}$ is better than the post-operative ocular imaging system $MTF_{n-1}$, the post-operative ocular imaging system $MTF_{n-1}$ is considered to be the best post-operative ocular imaging system MTF. Hence, the corneal ablation amount corresponding to the best post-operative ocular imaging system $MTF_{n-1}$ is determined to be the corneal ablation data that will be actually used in surgery (STEP 12). On the other hand, if the post-operative ocular imaging system $MTF_n$ is better than the post-operative ocular imaging system $MTF_{n-1}$, the corneal ablation amount is further changed by the predetermined amount to obtain the post-operative ocular imaging system MTF. This calculation is repeated until the post-operative ocular imaging system $MTF_{n-1}$ is better than the post-operative ocular imaging system $MTF_n$.

The above operation is done regarding every minute region of the corneal surface to obtain the corneal ablation amount that corrects the standard data about the corneal shape in a manner to achieve the best post-operative ocular imaging system MTF in each minute region. The corneal ablation data obtained thereby is determined as the data used in surgery.

The minute regions used to obtain the post-operative ocular imaging system MTF ensuring the best post-operative retinal image are the regions that can be ablated using the corneal surgery apparatus 3 selectively (in this preferred embodiment, they are the regions divided by the dividing mask 303 or the circular regions formed when the aperture mask 306 is gradually changed). In addition, in the calculation operation, the predetermined amount of corneal ablation to be changed is the amount that will be ablated by the corneal surgery apparatus 3 with one scanning or one shot of the excimer laser beam upon surgery. Further, in the case the ablation amount is changed in one minute region, the corneal ablation amount is obtained as follows: The corneal ablation amount in the adjacent minute regions is changed as well in order to allow the ablated surfaces of the adjacent minute regions to be connected smoothly.

As described above, once the post-operative ocular imaging system MTF ensuring the best post-operative retinal image and the corresponding data about the corneal ablation amount under that condition are obtained, the CPU 40 uses the above expression (1) to obtain the post-operative visual system MTF (the intended post-operative visual system MTF) from the obtained data about the post-operative ocular imaging system MTF and the pre-operative retina-brain system MTF (the data about the pre-operative retina-brain system MTF are considered to remain unaffected by surgery) (STEP 13). Then, the post-operative visual acuity of the eye E is estimated based on the thus obtained post-operative visual system MTF (STEP 14). The CPU 40 looks up a preliminary stored table of visual acuity which provides visual acuity in correspondence with the visual system MTF in order to retrieve visual acuity corresponding to the obtained post-operative visual system MTF. The retrieved visual acuity is displayed on the monitor 41 as the estimation of the post-operative visual acuity. Here, the visual acuity table stored in the memory 43 may be the table in which, for example, visual acuity corresponds to discriminating threshold of modulation transfer (the reciprocal of the fringe pitch) at a specific contrast value. As long as the correlation therebetween is known, visual acuity is obtained through arithmetic operation.

Since the estimation of the post-operative visual acuity is displayed on the monitor 41, the operator can inform the patient of the visual acuity in a pre-operative counselling asking for patient's informed consent. In addition, from the relation between the estimated visual acuity and the MTF data about the retina-brain system MTF, it is possible to make sure whether functions of the systems following the retina are normal or deteriorated. This allows to see the possibility of how much the patient's visual acuity is improved by refractive surgery. By giving the patient the information, surgery can be performed at the patient's consent.

In the case of performing corneal ablation surgery, the control unit 330 controls the laser source 301 and each of the driving units 331–334 in accordance with the corneal ablation data obtained by the computer unit 4 (the CPU 40) in order to carry out laser irradiation. In this way, not only paraxial influence but also influence by marginal rays to the image is taken into account and therefore the cornea can be ablated to change (alter) the shape to achieve the finest retinal image.

In this preferred embodiment, each measurement data obtained by the corneal shape analysis apparatus 1 and the MTF measurement apparatus 2 are transferred to the computer unit 4 and the computer unit 4 performs estimation of the post-operative MTF, the post-operative visual acuity and the like. However, it is possible to constitute one apparatus by combining more the two separate apparatuses into one. Further, there are various other schemes known to obtain each measurement data that are necessary for implementing the present invention. It is apparent that those variations are included in the scope of the present invention.

Further, it is also possible to obtain the ocular imaging system MTF through measurement of a fundus reflected image. That is, by causing a liner image to be formed on the retina or by projecting a spatial frequency chart, its reflected image is measured. The ocular imaging system MTF may be obtained from the measurement result. However, the MTF obtained through measurement of the reflected image is the round trip property to the ocular imaging system. Besides that, the reflecting property of the retina influenced the MTF. Due to these reasons, there is a set back that the MTF may not be the MTF solely of the imaging system. Accordingly, as in the above preferred embodiment, the ocular imaging system MTF is better to be obtained from the visual system MTF and the retina-brain MTF.

As described above, in accordance with the present invention, the post-operative state of the patient's eye is estimated so that surgery is performed at the patient's consent. In addition, the optimum corneal ablation data are obtained in consideration of the quality of the retinal image and therefore the corneal refractive surgery may be performed more adequately.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus used in refractive surgery to change a radius of curvature of a cornea, the apparatus comprising:

first input means for inputting data about a pre-operative corneal shape of a patient's eye;

second input means for inputting data about an intended post-operative corneal shape of the eye;

third input means for inputting data about a pre-operative MTF of an ocular imaging system of the eye; and arithmetic means for obtaining an intended post-operative MTF of the ocular imaging system of the eye based on each inputted data.

2. The ophthalmic apparatus according to claim 1, further comprising:

means for inputting correction amount data of the eye; and means for obtaining the data about the intended post-operative corneal shape based on the inputted correction amount data and the inputted pre-operative corneal shape, and wherein the second input means inputs the obtained data about the intended post-operative corneal shape into the arithmetic means.

3. The ophthalmic apparatus according to claim 2, further comprising eye refractive power measurement means for obtaining data about eye refractive power of the eye, and wherein the means for inputting correction amount data inputs the obtained data about the eye refractive power as the correction amount data.

4. The ophthalmic apparatus according to claim 1, further comprising:

means for inputting data about a pre-operative MTF of a visual system and data about a pre-operative MTF of a retina-brain system of the eye; and means for obtaining the data about the pre-operative MTF of the ocular imaging system based on the inputted data about the pre-operative MTF of the visual system and the inputted data about the pre-operative MTF of the retina-brain system, and wherein the third input means inputs the obtained data about the pre-operative MTF of the ocular imaging system into the arithmetic means.

5. The ophthalmic apparatus according to claim 4, further comprising MTF measurement means for obtaining the data about the MTF of the visual system and the data about the MTF of the retina-brain system, and wherein the means for inputting MTF data inputs the obtained data about the pre-operative MTF of the visual system and the obtained data about the pre-operative MTF of the retina-brain system.

6. The ophthalmic apparatus according to claim 1, further comprising corneal shape analysis means for obtaining the corneal shape of the eye, and wherein the first input means inputs the obtained data about the pre-operative corneal shape.

7. The ophthalmic apparatus according to claim 1, wherein the arithmetic means includes:

means for obtaining a pre-operative MTF of the cornea of the eye based on the inputted data about the pre-operative corneal shape;

means for obtaining a pre-operative MTF of an intraocular optical system of the eye based on the obtained pre-operative MTF of the cornea and the inputted pre-operative MTF of the ocular imaging system;

means for obtaining an intended post-operative MTF of the cornea of the eye based on the inputted data about the intended post-operative corneal shape; and means for obtaining the intended post-operative MTF of the ocular imaging system based on the obtained pre-operative MTF of the intraocular optical system and the intended post-operative MTF of the cornea obtained thereby.

8. The ophthalmic apparatus according to claim 1, further comprising:

means for inputting data about a pre-operative MTF of a retina-brain system of the eye; and means for estimating post-operative visual acuity of the eye based on the inputted pre-operative MTF of the retina-brain system and the intended post-operative MTF of the ocular imaging system obtained thereby.

9. The ophthalmic apparatus according to claim 8, wherein the means for estimating the visual acuity includes:

means for obtaining an intended post-operative MTF of the visual system of the eye based on the pre-operative MTF of the retina-brain system and the intended post-operative MTF of the ocular imaging system;

a memory containing a visual acuity table which provides visual acuity in correspondence with the MTF of the visual system; and means for estimating the post-operative visual acuity based on the intended post-operative MTF of the visual system and the stored visual acuity table.

10. The ophthalmic apparatus according to claim 1, further comprising means for obtaining corneal ablation data of the eye based on comparison of intended post-operative MTFs of the ocular imaging system that are obtained by modifying the data about the intended post-operative corneal shape.

11. The ophthalmic apparatus according to claim 10, wherein the second input means inputs, as the data about the intended post-operative corneal shape, each data obtained through increasing or decreasing a corneal ablation amount in each of minute regions into which an ablation region is divided, and the means for obtaining corneal ablation data obtains the corneal ablation data in a manner to achieve a best outcome through comparison of the intended post-operative MTFs of the ocular imaging system.

12. The ophthalmic apparatus according to claim 10, further comprising:

an irradiation optical system including a laser source for emitting a laser beam ablating the cornea and a change unit for selectively changing a region irradiated by the emitted laser beam; and control means for controlling at least one of the laser source and the change unit based on the obtained corneal ablation data.

13. An ophthalmic apparatus used in refractive surgery to change a radius of curvature of a cornea, the apparatus comprising:

a corneal shape analysis unit which obtains data about a corneal shape of a patient's eye;

an MTF measurement unit which obtains data about an MTF of a visual system and data about an MTF of a retina-brain system of the eye;

an input unit which inputs data about an intended post-operative corneal shape of the eye; and an arithmetic unit which obtains a pre-operative MTF of the cornea of the eye based on the obtained data about a pre-operative corneal shape, a pre-operative MTF of an ocular imaging system of the eye based on the obtained data about a pre-operative MTF of the visual system and the obtained data about a pre-operative MTF of the retina-brain system, a pre-operative MTF of an intraocular optical system of the eye based on the obtained pre-operative MTF of the cornea and the obtained pre-operative MTF of the ocular imaging system, an intended post-operative MTF of the cornea of the eye based on the inputted data about the intended post-operative corneal shape, and an intended post-operative MTF of the ocular imaging system of the eye based on the obtained pre-operative MTF of the intraocular optical system and the intended post-operative MTF of the cornea obtained thereby.

14. The ophthalmic apparatus according to claim 13, wherein the input unit inputs correction amount data of the eye as the data about the intended post-operative corneal shape, and the arithmetic unit obtains the intended post-operative MTF of the cornea based on the inputted correction amount data.

15. The ophthalmic apparatus according to claim 14, further comprising an eye refractive power measurement unit which obtains data about eye refractive power of the eye, and wherein the input unit inputs the obtained data about the eye refractive power as the correction amount data.

16. The ophthalmic apparatus according to claim 13, wherein the arithmetic unit further estimates post-operative visual acuity of the eye based on the obtained pre-operative MTF of the retina-brain system and the intended post-operative MTF of the ocular imaging system obtained thereby.

17. The ophthalmic apparatus according to claim 13, wherein the arithmetic unit further obtains corneal ablation data of the eye based on comparison of intended post-operative MTFs of the ocular imaging system that are obtained by modifying the data about the intended post-operative corneal shape.

18. An ophthalmic apparatus used in refractive surgery to change a radius of curvature of a cornea, the apparatus comprising:

a memory containing a program for obtaining an intended post-operative MTF of an ocular imaging system of the eye based on data about a pre-operative corneal shape, data about an intended post-operative corneal shape and data about a pre-operative MTF of the ocular imaging system of the eye; and an arithmetic unit which performs arithmetic operation in accordance with the program.

19. The ophthalmic apparatus according to claim 18, wherein the program includes the steps of:

obtaining a pre-operative MTF of the cornea of the eye based on the data about the pre-operative corneal shape;

obtaining a pre-operative MTF of an intraocular optical system of the eye based on the obtained pre-operative MTF of the cornea and the pre-operative MTF of the ocular imaging system;

obtaining an intended post-operative MTF of the cornea of the eye based on the data about the intended post-operative corneal shape; and obtaining the intended post-operative MTF of the ocular imaging system based on the obtained pre-operative MTF of the intraocular optical system and the intended post-operative MTF of the cornea obtained thereby.

20. The ophthalmic apparatus according to claim 18, wherein the program further includes the step of obtaining the pre-operative MTF of the ocular imaging system based on a pre-operative MTF of a visual system and a pre-operative MTF of a retina-brain system.

21. The ophthalmic apparatus according to claim 18, wherein the program further includes the step of estimating post-operative visual acuity of the eye based on a pre-operative MTF of a retina-brain system and the intended post-operative MTF of the ocular imaging system of the eye obtained thereby.

22. The ophthalmic apparatus according to claim 18, wherein the program further includes the step of obtaining corneal ablation data of the eye based on comparison of intended post-operative MTFs of the ocular imaging system that are obtained by modifying the data about the intended post-operative corneal shape.

* * * * *